United States Patent
Kawata et al.

(10) Patent No.: US 11,684,321 B2
(45) Date of Patent: Jun. 27, 2023

(54) RADIATION DIAGNOSTIC DEVICE COMPRISING A FIRST DETECTOR FOR DETECTING CHERENKOV LIGHT AND A SECOND DETECTOR FOR DETECTING SCINTILLATION LIGHT, CORRECTION METHOD FOR COMPTON SCATTERING, AND NON-TRANSITORY COMPUTER-READABLE MEDIUM

(71) Applicant: CANON MEDICAL SYSTEMS CORPORATION, Otawara (JP)

(72) Inventors: Go Kawata, Nagareyama (JP); Ryo Okuda, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 40 days.

(21) Appl. No.: 17/412,734

(22) Filed: Aug. 26, 2021

(65) Prior Publication Data
US 2022/0065803 A1 Mar. 3, 2022

(30) Foreign Application Priority Data

Aug. 26, 2020 (JP) .................................. 2020-142909
Aug. 17, 2021 (JP) .................................. 2021-132980

(51) Int. Cl.
*A61B 6/03* (2006.01)
*G01T 1/16* (2006.01)
(Continued)

(52) U.S. Cl.
CPC ............ *A61B 6/037* (2013.01); *A61B 6/4241* (2013.01); *A61B 6/4258* (2013.01);
(Continued)

(58) Field of Classification Search
CPC ......... A61B 6/037; A61B 6/42; A61B 6/4208; A61B 6/4225; A61B 6/4241;
(Continued)

(56) References Cited

U.S. PATENT DOCUMENTS 3,955,088 A * 5/1976 Muehllehner ......... G01T 1/2985
250/369
7,045,789 B2 5/2006 Ogawa et al.
(Continued)

FOREIGN PATENT DOCUMENTS

| EP | 3 859 400 A1 | 8/2021 |
| JP | 2002-116256 A | 4/2002 |
| JP | 2017-191086 A | 10/2017 |
| WO | WO 2010/085150 A1 | 7/2010 |

OTHER PUBLICATIONS

R. Robertson et al., Optical imaging of Cerenkov light generation from positron-emitting radiotracers, Phys. Med. Biol. 54 N355-N365 (2009). (Year: 2009).*

(Continued)

*Primary Examiner* — Allen C. Ho
(74) *Attorney, Agent, or Firm* — Oblon, McClelland, Maier & Neustadt, L.L.P.

(57) ABSTRACT

A radiation diagnostic device according to an aspect of the present invention includes a first detector, a second detector, and processing circuitry. The first detector detects Cherenkov light that is generated when radiation passes. The second detector is disposed to be opposed to the first detector on a side distant from a generation source of the radiation, and detects energy information of the radiation. The processing circuitry specifies Compton scattering events detected by the second detector, and determines an event corresponding to an incident channel among the specified Compton scattering events based on a detection result obtained by the first detector.

16 Claims, 9 Drawing Sheets

(51) Int. Cl.
  *G01T 1/20* (2006.01)
  *G01T 1/22* (2006.01)
  *G01T 1/29* (2006.01)
  *A61B 6/00* (2006.01)
  *G01N 23/20066* (2018.01)
  *G01T 1/164* (2006.01)

(52) U.S. Cl.
  CPC .......... *A61B 6/4266* (2013.01); *A61B 6/4275* (2013.01); *A61B 6/482* (2013.01); *A61B 6/483* (2013.01); *A61B 6/5205* (2013.01); *A61B 6/5282* (2013.01); *G01N 23/20066* (2013.01); *G01T 1/1642* (2013.01); *G01T 1/2006* (2013.01); *G01T 1/2018* (2013.01); *G01T 1/20181* (2020.05); *G01T 1/20182* (2020.05); *G01T 1/22* (2013.01); *G01T 1/2907* (2013.01); *G01T 1/2914* (2013.01); *G01T 1/2985* (2013.01); *G01N 2223/108* (2013.01)

(58) Field of Classification Search
  CPC ... A61B 6/4258; A61B 6/4266; A61B 6/4275; A61B 6/482; A61B 6/483; A61B 6/52; A61B 6/5205; A61B 6/5211; A61B 6/5282; A61B 6/5258; G01T 1/1642; G01T 1/20; G01T 1/2006; G01T 1/2018; G01T 1/20181; G01T 1/20182; G01T 1/22; G01T 1/29; G01T 1/2907; G01T 1/2914; G01T 1/2985; G01T 1/20183; G01T 1/2921; G01T 1/2928; G01T 1/2935
  USPC ................ 378/19, 5, 98.8, 98.9; 250/363.04, 250/370.09, 370.1, 370.11
  See application file for complete search history.

(56) References Cited

U.S. PATENT DOCUMENTS

| | | | | |
|---|---|---|---|---|
| 7,897,925 | B2* | 3/2011 | Goldberg | G01T 1/2935 |
| | | | | 250/397 |
| 8,674,312 | B2* | 3/2014 | Szupryczynski | G01T 1/22 |
| | | | | 250/366 |
| 10,274,610 | B2* | 4/2019 | Nelson | G01T 1/2002 |
| 10,281,594 | B2* | 5/2019 | Benlloch Baviera | G01T 1/17 |
| 10,365,383 | B2* | 7/2019 | Nelson | A61B 8/4416 |
| 10,509,135 | B2* | 12/2019 | Nelson | A61B 6/4258 |
| 10,816,682 | B2* | 10/2020 | Ota | G01T 1/363 |
| 10,895,651 | B2* | 1/2021 | Watanabe | G01T 1/2985 |
| 11,448,780 | B2* | 9/2022 | Ilisie | G01T 1/1642 |
| 2004/0031926 | A1 | 2/2004 | Ogawa et al. | |
| 2018/0252825 | A1 | 9/2018 | Benlloch Baviera et al. | |
| 2019/0324161 | A1 | 10/2019 | Ota | |
| 2019/0353808 | A1 | 11/2019 | Watanabe et al. | |
| 2020/0033486 | A1 | 1/2020 | Nelson et al. | |
| 2020/0326438 | A1 | 10/2020 | Ota et al. | |

OTHER PUBLICATIONS

Extended European Search Report dated Dec. 17, 2021 in European Patent Application No. 21193199.3, 11 pages.

D. Consuegra, et al., "Improving the Cherenkov Based PET Performance Using Multi-Layer Detectors," 2019 IEEE Nuclear Science Symposium and Medical Imaging Conference (NSS/MIC), XP033747990, 2019, 5 pages.

Hyeok-jun Choe, et al., "Development of a New Position Decoder Circuit for PET Consisting of GAPD Arrays to Recover Inter-crystal Scattered Events," 2013 IEEE Nuclear Science Symposium and Medical Imaging Conference (2013 NSS/MIC), XP032601378, 2013, 3 pages.

* cited by examiner

RADIATION DIAGNOSTIC DEVICE COMPRISING A FIRST DETECTOR FOR DETECTING CHERENKOV LIGHT AND A SECOND DETECTOR FOR DETECTING SCINTILLATION LIGHT, CORRECTION METHOD FOR COMPTON SCATTERING, AND NON-TRANSITORY COMPUTER-READABLE MEDIUM

CROSS-REFERENCE TO RELATED APPLICATIONS

This application is based upon and claims the benefit of priority from Japanese Patent Application No. 2020-142909, filed on Aug. 26, 2020 and Japanese Patent Application No. 2021-132980, filed on Aug. 17, 2021; the entire contents of which are incorporated herein by reference.

FIELD

Embodiments described herein relate generally to a radiation diagnostic device, a correction method for Compton scattering.

BACKGROUND

As a radiation diagnostic device, there is known a positron emission tomography (PET) device. The PET apparatus specifies a pair annihilation position of a positron by detecting scintillation light that is generated when a pair of pair annihilation gamma rays are incident on a scintillator, the pair of pair annihilation gamma rays that are pair-produced when the positron emitted by a radiation medical supply labeled with a positron emitting nuclide is pair-annihilated with an electron, and generates a medical image by using the pair annihilation position.

However, the scintillation light is light that is re-emitted along with a transition process in which an excited state generated by the pair annihilation gamma rays returns to a ground state over time, so that a response speed thereof is relatively low, and an error may be caused in specification of the pair annihilation position of the positron. Thus, for example, it can be considered that the pair annihilation position of the positron is specified by using both of a detector for detecting scintillation light and a detector for detecting Cherenkov light.

As a result, by using both of a Cherenkov light detector having excellent time resolution and a scintillation light detector having excellent energy resolution, image quality of the radiation diagnostic device can be improved.

In a case of using both of the detector for detecting scintillation light and the detector for detecting Cherenkov light, similarly to a case of using only the detector for detecting scintillation light, there is an event of causing a photoelectric effect after Compton scattering is caused once in the detector for detecting scintillation light. If such an event of causing the photoelectric effect after Compton scattering is appropriately considered to be imaged, the image quality can be expected to be further improved.

DETAILED DESCRIPTION

A radiation diagnostic device according to an aspect of the present invention includes first detectors, second detectors, and processing circuitry. The first detector detects Cherenkov light that is generated when radiation passes. The second detector is disposed to be opposed to the first detector on a side more distant from a generation source of the radiation, and detects energy information of the radiation. The processing circuitry specifies Compton scattering events detected by the second detector, and determines an event corresponding to an incident channel among the specified Compton scattering events based on a detection result obtained by the first detector.

The following describes the radiation diagnostic device according to the embodiments in detail with reference to the drawings.

First Embodiment

Figure 1:
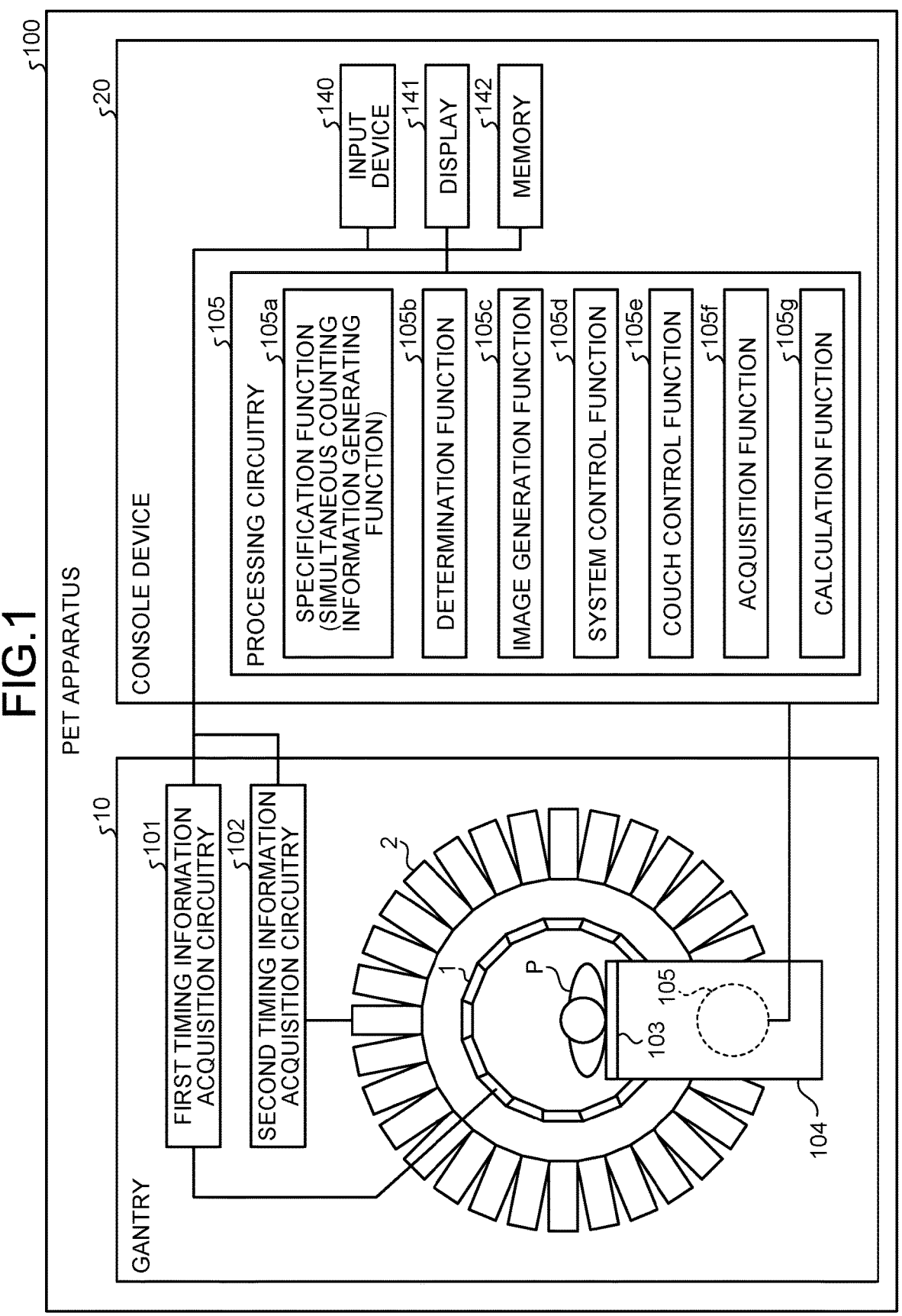
FIG. 1 is a diagram illustrating a configuration of a radiation diagnostic device according to an embodiment.

First, with reference to FIG. 1, the following describes a configuration of the radiation diagnostic device according to an embodiment by exemplifying a PET apparatus.

FIG. 1 is a diagram illustrating a configuration of a PET apparatus 100 as the radiation diagnostic device according to the embodiment. As illustrated in FIG. 1, the PET apparatus 100 according to the embodiment includes a gantry 10 and a console device 20.

The gantry 10 detects a pair of pair annihilation gamma rays emitted from a positron in a subject P by first detectors 1 for detecting Cherenkov light and second detectors 2 for detecting scintillation light that are disposed to surround a periphery of the subject P in a ring shape. The gantry 10 generates counting information from output signals of the first detectors 1 and the second detectors 2 by first timing information acquisition circuitry 101 and second timing information acquisition circuitry 102.

More specifically, the gantry 10 includes a couchtop 103, a couch 104, a couch driving unit 105, the first detectors 1 for detecting Cherenkov light, the second detectors 2 for detecting scintillation light, the first timing information acquisition circuitry 101 for generating counting information from the first detectors 1, and the second timing information acquisition circuitry 102 for generating counting information from the second detectors 2.

The first detector 1 is a detector that acquires counting information related to the pair annihilation gamma rays emitted from the positron in the subject P by detecting Cherenkov light as light of a shock wave that is generated when a charged particle moves at a higher speed than a phase speed of light in a medium, the charged particle being generated when the pair annihilation gamma rays emitted from the positron in the subject P interacts with an internal light emitting body (radiator). That is, the first detector 1 detects Cherenkov light that is generated when radiation passes.

The first detector 1 as a detector for pair annihilation gamma rays using Cherenkov light is disadvantageous as compared with a detector for pair annihilation gamma rays using scintillation light in view of sensitivity to energy. However, Cherenkov light is generated in a very short time as compared with scintillation light, and has a good response characteristic, so that the first detector 1 as a detector using a method of detecting Cherenkov light has a characteristic of being advantageous in view of time resolution as compared with a detector using a method of detecting scintillation light.

In other words, the first detector 1 as a detector for detecting Cherenkov light has a characteristic of being advantageous in view of time resolution as compared with the second detector 2 as a detector for detecting scintillation light. On the other hand, the second detector 2 as a detector for detecting scintillation light has a characteristic of being advantageous in view of energy resolution as compared with the first detector 1 as a detector for detecting Cherenkov light.

Thus, the radiation diagnostic device according to the embodiment generates the counting information using the first detector 1 and the second detector 2. Due to this, the counting information can be generated while maintaining energy resolution and high time resolution.

Returning to the description about the configuration of the first detector 1, the first detector 1 includes, for example, a light emitting body (radiator) constituted of a medium that generates Cherenkov light by interacting with the pair annihilation gamma rays as radiation emitted from the positron in the subject P, and a light detection element that detects the generated Cherenkov light.

As the light emitting body included in the first detector 1, for example, it is possible to use a medium containing an atom having a large atomic number that has a property of easily causing a photoelectric effect due to interaction of incident radiation, and hardly generating scintillation light to be noise, for example, bismuth germanium oxide (BGO), or a lead compound such as lead glass ($SiO_2+PbO$), lead fluoride ($PbF_2$), and PWO ($PbWO_4$). In other words, the light emitting body in the first detector 1 is constituted of a medium that easily causes a photoelectric effect but suppresses scintillation caused by radiation.

The light detection element detects the generated Cherenkov light. A light detection element is a silicon photomultiplier (SiPM) that is an Avalanche Photo Diode (APD) array in which an individual pixel size is reduced to be about several tens of microns, for example, and operates in a Geiger mode. By way of another example, the light detection element is constituted of a plurality of pixels that perform photoelectric conversion, and each of the pixels is constituted of a Single Photon Avalanche Diode (SPAD), for example.

The second detector 2 is a detector that detects radiation by detecting scintillation light (fluorescence) as light that is re-emitted when a substance in an excited state makes transition to a ground state again, the substance that has been caused to be in the excited state when an annihilation gamma ray emitted from the positron in the subject P interacts with the light emitting body (scintillator). The second detector 2 is also a detector that detects energy information of radiation of the annihilation gamma ray emitted from the positron in the subject P.

A thickness of a light emitting body in the first detector 1 may be designed to be smaller than a thickness of a scintillator disposed in the second detector 2, for example, so that a gamma ray does not lose total energy in the light emitting body. Due to this, the pair annihilation gamma rays that are pair-produced can be incident on the second detector 2 while generating Cherenkov light in the first detector 1 and holding most of the energy, and can generate scintillation light in the second detector 2.

A pixel size of the light emitting body in the first detector 1 can be caused to be smaller than a pixel size of the scintillator in the second detector 2, for example. Due to this, position resolution of data obtained from the first detector 1 can be relatively improved. Furthermore, a detector row length of the first detectors may be configured to be shorter than a detector row length of the second detectors.

The second detector 2 is disposed to be opposed to the first detector 1 for detecting Cherenkov light on a side distant from a generation source of the radiation, that is, the annihilation gamma ray emitted from the positron in the subject P. By way of example, the second detectors 2 are disposed while being divided into a plurality of detector blocks to further surround, in a ring shape, the periphery of the first detectors 1 that are disposed to surround the periphery of the subject P in a ring shape. By way of example, the second detectors 2 are ring-shaped detectors similarly to the first detectors 1, and a diameter of the second detectors 2 is larger than a diameter of the first detectors 1.

As described above, scintillation light is generated in a later process as compared with generation of Cherenkov light. On the other hand, most of the energy of the annihilation gamma rays is converted into scintillation light, so that the second detector 2 using scintillation light is more advantageous than the first detector 1 using Cherenkov light in view of energy measurement for the annihilation gamma rays.

The second detector 2 is constituted of a plurality of pixels. Herein, one pixel of the detector indicates a minimum separation unit of the position resolution of the detector. For example, in a case in which a plurality of light detection elements respectively detect pieces of scintillation light generated at different positions, each of the light detection elements becomes a detector of one pixel. In contrast, in a case in which each of the light detection elements detects scintillation light generated at the same position, the light detection elements become a detector of one pixel in total.

In the embodiment, similarly to the first detector 1, one light detection element constituting the second detector 2 may be configured as a multi-pixel light detection element.

FIG. 1 illustrates an example in which the second detector 2 includes a plurality of detector blocks. However, one pixel in FIG. 2 means a pixel unit by which a generation position of Cherenkov light can be separated, and may be a unit smaller than a unit of the detector block illustrated in FIG. 1. That is, each detector block of the second detector 2 configured in a ring shape illustrated in FIG. 1 may be constituted of a plurality of pixels.

Subsequently, an example of a specific configuration of the second detector 2 is an Anger-type detector using a photon counting scheme, which includes a scintillator, a light detection element, and a light guide (not illustrated), for example.

The scintillator converts an incident annihilation gamma ray emitted from a positron in the subject P into scintillation light (scintillation photons, optical photons) to be output. The scintillator is, for example, made of a scintillator crystal appropriate for TOF measurement and energy measurement such as Lanthanum Bromide (LaBr3), Lutetium Yttrium Oxyorthosilicate (LYSO), Lutetium Oxyorthosilicate (LSO), Lutetium Gadolinium Oxyorthosilicate (LGSO), or BGO, and is two-dimensionally arranged, for example.

As the light detection element, for example, the Silicon photomultiplier (SiPM) described above or a photomultiplier tube is used. The photomultiplier tube includes a photocathode that receives scintillation light and generates a photoelectron, a multi-stage dynode that gives an electric field for accelerating the generated photoelectron, and an anode serving as an outlet of electrons, and multiplies scintillation light output from the scintillator to be converted into an electric signal.

The light guide is made of a plastic material and the like having excellent light transmittivity, and transmits the scintillation light output from the scintillator to the light detection element such as the SiPM or the photomultiplier tube.

Subsequently, the following describes other configurations.

The first timing information acquisition circuitry 101 generates counting information from an output signal of the first detector 1, and stores the generated counting information in a memory 142 of the console device 20. Although not illustrated in FIG. 1, the first detector 1 is partitioned into a plurality of blocks, and includes the first timing information acquisition circuitry 101 for each block.

The first timing information acquisition circuitry 101 converts the output signal from the first detector 1 into digital data, and generates the counting information. The counting information includes a detection position and a detection time of the annihilation gamma ray. For example, the first timing information acquisition circuitry 101 specifies a plurality of light detection elements that have converted Cherenkov light into an electric signal at the same timing. The first timing information acquisition circuitry 101 then calculates a position of the center of gravity by using a position of each of specified light detection elements and strength of the electric signal, and specifies a detection element number (P) indicating a position of a radiator on which the annihilation gamma ray is incident.

The first timing information acquisition circuitry 101 specifies a detection time (T) at which the first detector 1 detects Cherenkov light generated by the annihilation gamma ray. The detection time (T) may be an absolute time, or may be an elapsed time from a start point of photographing. In this way, the first timing information acquisition circuitry 101 generates the counting information including the detection element number (P) and the detection time (T).

The second timing information acquisition circuitry 102 generates the counting information from the output signal of the second detector 2, and stores the generated counting information in the memory 142 of the console device 20. Similarly to the case of the first detector 1, the second detector 2 is partitioned into a plurality of blocks, and includes the second timing information acquisition circuitry 102 for each block.

The second timing information acquisition circuitry 102 converts the output signal of the second detector 2 into digital data, and generates the counting information. The counting information includes a detection position, an energy value, and a detection time of the annihilation gamma ray. For example, the second timing information acquisition circuitry 102 specifies a plurality of light detection elements that have converted scintillation light into an electric signal at the same timing. The second timing information acquisition circuitry 102 then specifies a scintillator number (P) indicating a position of the scintillator on which the annihilation gamma ray is incident. The scintillator position at which the annihilation gamma ray is incident may also be specified by calculating the center of gravity based on the position of each light detection element and the strength of the electric signal. In a case in which respective element sizes of the scintillator and the light detection element correspond to each other, the scintillator corresponding to the light detection element from which an output is obtained may be specified as the scintillator position at which the annihilation gamma ray is incident.

The second timing information acquisition circuitry 102 also specifies an energy value (E) of the annihilation gamma ray incident on the second detector 2 by integrating strengths of electric signals output from the respective light detection elements. The second timing information acquisition circuitry 102 also specifies the detection time (T) at which the second detector 2 detects the scintillation light caused by the annihilation gamma ray. The detection time (T) may be an absolute time, or may be an elapsed time from the start point of photographing. In this way, the second timing information acquisition circuitry 102 generates the counting information including the scintillator number (P), the energy value (E), and the detection time (T).

Each of the first timing information acquisition circuitry 101 and the second timing information acquisition circuitry 102 is implemented, for example, by a central processing unit (CPU), a graphical processing unit (GPU), or a circuit such as an application specific integrated circuit (ASIC) or a programmable logic device (for example, a simple programmable logic device (SPLD), a complex programmable logic device (CPLD), and a field programmable gate array (FPGA)).

The couchtop 103 is a bed on which the subject P is placed, and is disposed on the couch 104. The couch driving unit 105 moves the couchtop 103 under control by a couch control function 105e of processing circuitry 105. For example, the couch driving unit 105 moves the subject P into a photographing port of the gantry 10 by moving the couchtop 103.

The console device 20 receives an operation on the PET apparatus 100 by an operator, controls photographing of a PET image, and reconstruct the PET image by using the counting information collected by the gantry 10. As illustrated in FIG. 1, the console device 20 includes the processing circuitry 105, an input device 140, a display 141, and the memory 142. Respective units included in the console device 20 are connected via a bus.

In the embodiment, each of processing functions performed by a specification function (simultaneous counting information generation function) 105a, a determination function 105b, an image generation function 105c, a system control function 105d, the couch control function 105e, an acquisition function 105f, and a calculation function 105g is stored in the memory 142 as a computer-executable program. The processing circuitry 105 is a processor that implements a function corresponding to each computer program by reading out the computer program from the memory 142 to be executed. In other words, the processing circuitry 105 that has read out each computer program is assumed to have each of the functions illustrated in the processing circuitry 105 of FIG. 1. Regarding FIG. 1, it is assumed that the single processing circuitry 105 implements the respective processing functions performed by the specification function (simultaneous counting information generation function) 105a, the determination function 105b, the image generation function 105c, the system control function 105d, the couch control function 105e, the acquisition function 105f, and the calculation function 105g. Alternatively, the processing circuitry 105 may be configured by combining a plurality of independent processors, and each of the processors may execute the computer program to implement the function. In other words, each of the functions described above may be configured as a computer program, and the one processing circuitry 105 may execute each computer program. By way of another example, a specific function may be implemented on a dedicated independent program execution circuit.

In FIG. 1, the specification function 105a, the determination function 105b, the image generation function 105c, the system control function 105d, the couch control function 105e, the acquisition function 105f, and the calculation function 105g are examples of a specification unit, a determination unit, an image generation unit, a system control unit, a couch control unit, an acquisition unit, and a calculation unit, respectively.

The word of "processor" used in the above description means, for example, a central processing unit (CPU), a graphical processing unit (GPU), or a circuit such as an application specific integrated circuit (ASIC) or a programmable logic device (for example, a simple programmable logic device (SPLD), a complex programmable logic device (CPLD), and a field programmable gate array (FPGA)). The processor implements the function by reading out the computer program stored in the memory 142 to be executed.

The processing circuitry 105 generates, by the specification function (simultaneous counting information generation function) 105a, the simultaneous counting information based on the counting information related to the first detector 1 acquired by the first timing information acquisition circuitry 101 and the counting information related to the second detector 2 acquired by the second timing information acquisition circuitry 102, and stores the generated simultaneous counting information in the memory 142.

As described later, the processing circuitry 105 performs processing related to Compton scattering correction by the specification function 105a and the determination function 105b. For example, the processing circuitry 105 specifies, by the specification function 105a, Compton scattering events detected by the second detector. The processing circuitry 105 determines, by the determination function 105b, an event corresponding to an incident channel among the specified Compton scattering events based on a detection result obtained by the first detector. Detailed processing performed by the specification function 105a, the determination function 105b, the acquisition function 105f, and the calculation function 105g will be described later.

The processing circuitry 105 reconstructs the PET image by the image generation function 105c. Specifically, the processing circuitry 105 reads out a time-series list of the simultaneous counting information stored in the memory 142 by the image generation function 105c, and reconstructs the PET image by using the read-out time-series list. The processing circuitry 105 also stores the reconstructed PET image in the memory 142.

The processing circuitry 105 performs overall control for the PET apparatus 100 by controlling the gantry 10 and the console device 20 by the system control function 105d. For example, the processing circuitry 105 controls, by the system control function 105d, photographing by the PET apparatus 100.

The processing circuitry 105 controls the couch driving unit 105 by the couch control function 105e.

The input device 140 is a mouse, a keyboard, or the like used by an operator of the PET apparatus 100 for inputting various instructions and various settings, and transfers the input various instructions and various settings to the processing circuitry 105. For example, the input device 140 is used for inputting an instruction for starting photographing.

The display 141 is a monitor and the like referred to by the operator, and displays a PET image or a respiration waveform of the subject, or displays a graphical user interface (GUI) for receiving various instructions and various settings from the operator under control by the processing circuitry 105.

The memory 142 stores various kinds of data used by the PET apparatus 100. The memory 142 is, for example, implemented by a semiconductor memory element such as a random access memory (RAM) and a flash memory, a hard disk, an optical disc, and the like. The memory 142 stores the counting information as information in which the scintillator number (P), the energy value (E), and the detection time (T) are associated with each other, the simultaneous counting information in which a group of the counting information is associated with a coincidence No. as a serial number of the simultaneous counting information, a reconstructed PET image, and the like.

Subsequently, the following describes generation of the simultaneous counting information in a case of not considering a Compton scattering event in the second detector with reference to FIG. 2.

Figure 2:
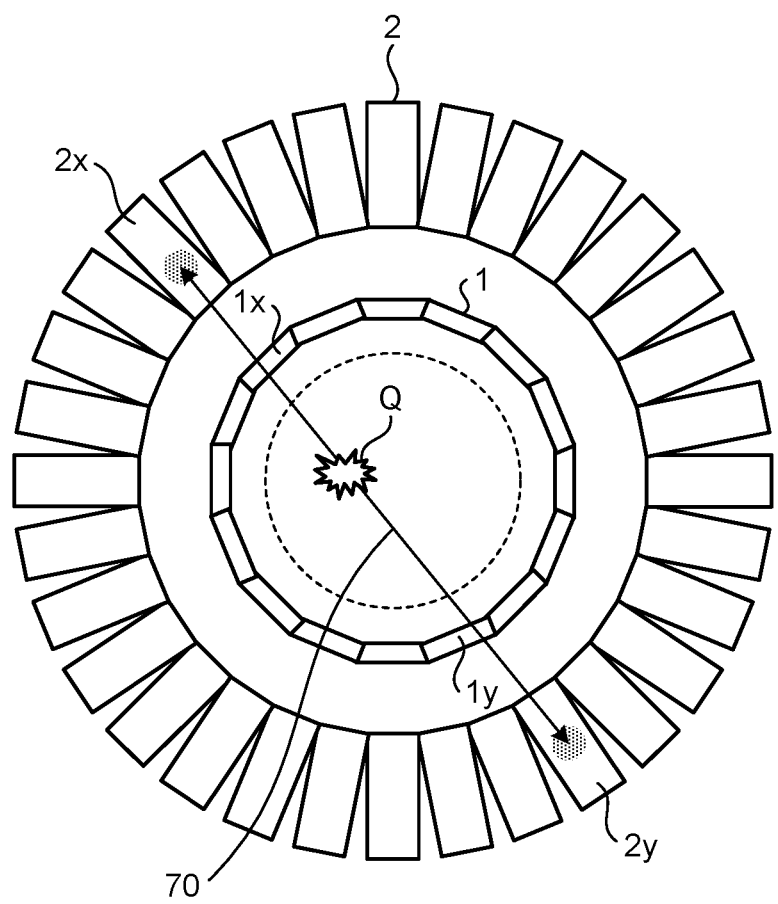
FIG. 2 is a diagram for explaining count processing performed by the radiation diagnostic device according to the first embodiment.

As illustrated in FIG. 2, it is assumed that Cherenkov light derived from a pair of gamma rays that are pair-produced from a pair annihilation point Q is detected by a detector 1x and a detector 1y as the first detectors 1 for detecting Cherenkov light, and scintillation light caused by the pair of gamma rays, along a line of response 70, that are pair-produced from the pair annihilation point Q is detected by a detector 2x and a detector 2y as the second detectors 2 for detecting scintillation light. In this case, the processing circuitry 105 generates, by the specification function 105a, the simultaneous counting information by using a pair of detectors as the first detectors 1, a pair of detectors as the second detectors 2, and data obtained from the two pairs of detectors.

As described later, momentum of the gamma rays is changed due to presence of a recoil electron when the pair of gamma rays generates Cherenkov light, so that trajectory of the gamma rays are actually deviated from initial trajectory of the gamma rays by a fine angle.

Subsequently, the following describes a background of the embodiment.

As a method for improving time resolution of the PET apparatus, there is known a method of using, for time-resolved measurement, Cherenkov light that is generated when a charged particle travels on a material. By way of example, there is known a Dual-ring type detector. In the Dual-ring type detector, an inner ring detects Cherenkov light to detect a timing of an event, and an outer ring detects scintillation light to detect energy information of the event. Due to this, Cherenkov light can be used for time-resolved measurement, and time resolution of the PET apparatus can be improved.

Figure 3:
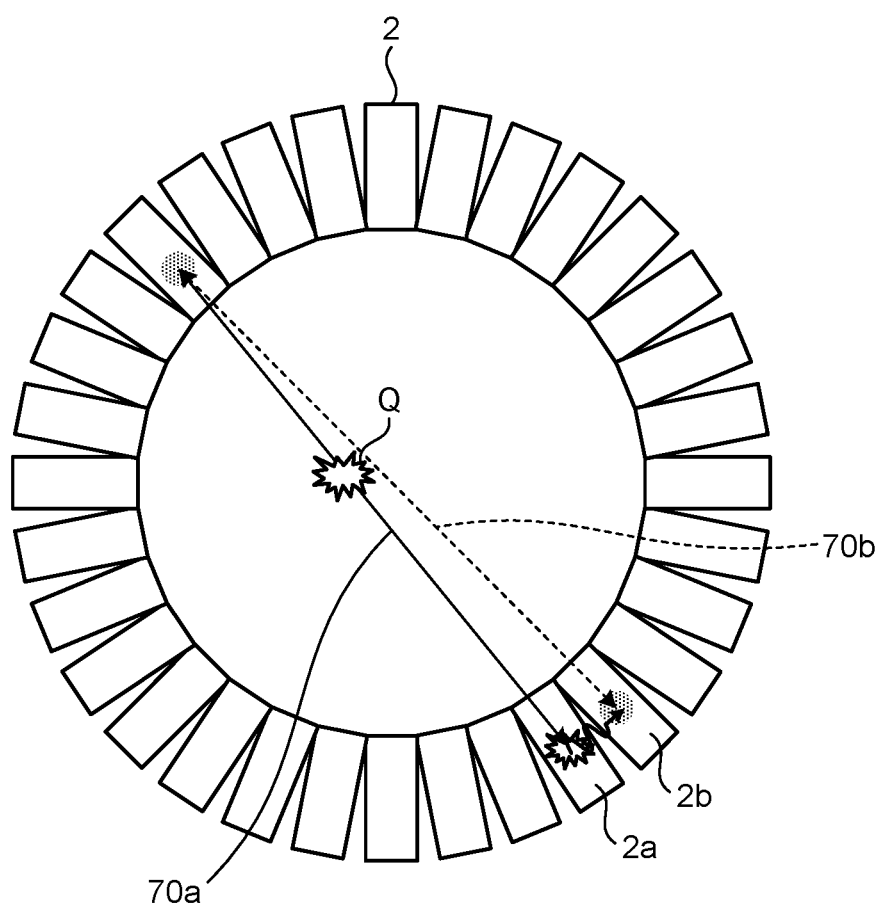
FIG. 3 is a diagram for explaining a background according to the embodiment.

It is known that the pair annihilation gamma rays are scattered in the scintillator due to Compton effect. When Compton scattering occurs in the scintillator, interaction may be caused in an adjacent scintillator different from an incident scintillator. For example, as illustrated in FIG. 3, one of the gamma rays that are pair-produced from the pair annihilation point Q causes Compton scattering in a detector 2a as one of the second detectors 2, and as a result, signals are observed in the detector 2a and the detector 2b.

Figure 4:
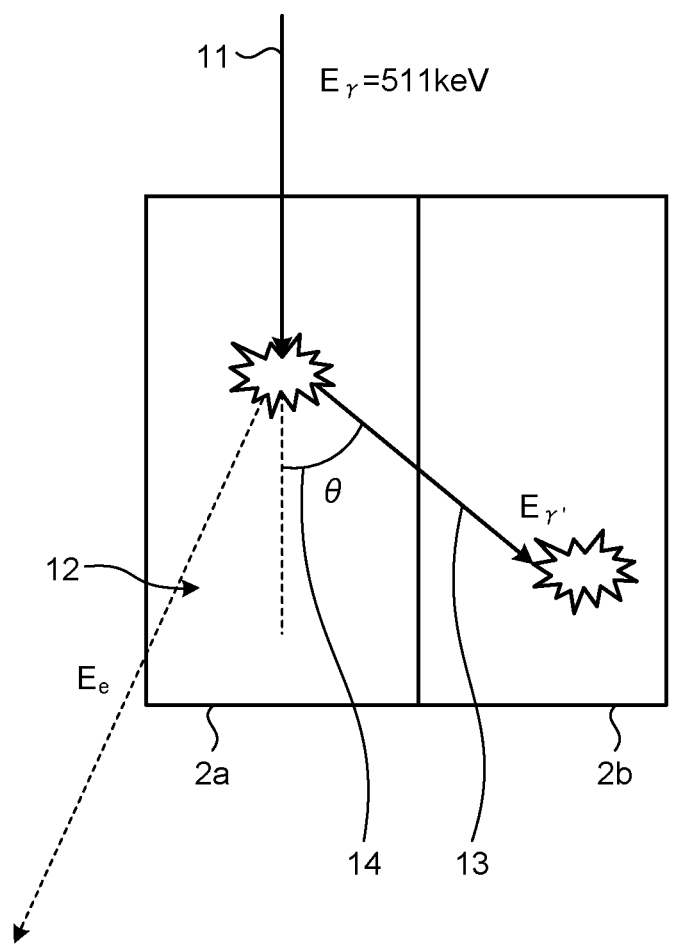
FIG. 4 is a diagram for explaining a background according to the embodiment.

FIG. 4 illustrates a schematic diagram of such a situation. As illustrated in FIG. 4, an incident gamma ray 11 that is incident on the second detector 2a interacts with an electron due to Compton scattering, and gives energy to the electron. As a result, energy of the electron is changed, and a recoil electron 12 is generated. In addition, since the incident gamma ray 11 has passed energy to the recoil electron 12, the energy of the incident gamma ray 11 is changed, and a gamma ray 13 after Compton scattering appears.

The recoil electron 12 passes energy to the detector 2a through various processes, and the incident gamma ray 11 passes energy to the detector 2b by a photoelectric effect. As a result, signals are observed in both of the detector 2a and the detector 2b. In this case, an accurate LOR can be estimated by finding that the gamma ray is incident earlier on which one of the detector 2a and the detector 2b in which the signal is observed.

Assuming that energy of the incident gamma ray 11 is $E_\gamma$, energy that is given to the recoil electron 12 by the incident gamma ray 11 along with Compton scattering is $E_e$, and energy of the gamma ray 13 after Compton scattering is $E_{\gamma'}$, the following expression (1) is established.

$$E_e + E_{\gamma'} = E_\gamma \quad (1)$$

In a case in which the incident gamma ray 11 is Compton-scattered by a stationary electron, energy of the recoil electron 12 after Compton scattering becomes equal to energy $E_e$ that is given to the recoil electron 12 by the incident gamma ray 11 along with Compton scattering.

It is known that the energy $E_e$ that is given to the recoil electron 12 by the incident gamma ray 11 along with Compton scattering is different depending on a scattering direction of the recoil electron, but has a maximum value. Actually, the energy $E_e$ that is given to the recoil electron 12 by the incident gamma ray 11 along with Compton scattering reaches the maximum value when the recoil electron is scattered in a direction opposite to the incident gamma ray 11, that is, at the time of back scattering, and a spectrum corresponding to the energy at this point is called a Compton edge. That is, the energy $E_e$ that is given to the recoil electron 12 by the incident gamma ray 11 is energy equal to or larger than 0, and equal to or smaller than energy corresponding to the Compton edge. Additionally, the energy $E_{\gamma'}$ of the gamma ray 13 after Compton scattering is energy equal to or larger than energy obtained by subtracting the energy corresponding to the Compton edge from the energy of the incident gamma ray 11, and is energy equal to or smaller than the energy of the incident gamma ray 11.

A specific expression of the energy $E_{\gamma'}$ of the gamma ray 13 after Compton scattering is given as the following expression (2) assuming that a mass of the electron is $m_0$, a light velocity is c, and a value of a scattering angle 14 is θ.

$$E_{\gamma'} = \frac{E_\gamma}{1 + \frac{E_\gamma}{m_0 c^2}(1 - \cos\theta)} \quad (2)$$

In an actual situation, the scattering angle 14 and an incident direction of the incident gamma ray 11 are unknown, so that it is unknown that which of the signal of the detector 2a and the signal of the detector 2b is a signal corresponding to an initial gamma ray incident position. As a result, an error may be caused in estimation of a line of response (LOR) (e.g., 70a or 70b in FIG. 3) in some cases.

In view of such a background, the radiation diagnostic device according to the first embodiment specifies the event corresponding to the incident channel among the Compton scattering events using information of the first detector for detecting Cherenkov light. Due to this, the incident position of the gamma ray at the time of Compton scattering can be estimated, and a more accurate LOR can be estimated. Accordingly, spatial resolution of the PET image can be improved.

Regarding FIG. 4, for simplifying the description, deviation of trajectories of the gamma rays that is caused when the pair annihilation gamma rays interact with the first detector 1 is not described. However, actually, as the recoil electron is generated when the pair annihilation gamma rays generate Cherenkov light in the first detector 1, the trajectories of the pair annihilation gamma rays after passing through the first detector 1 are deviated from the trajectories of the pair annihilation gamma rays before passing through the first detector 1 by a fine angle. In the embodiment, Compton correction is performed while considering such an effect.

Figure 5:
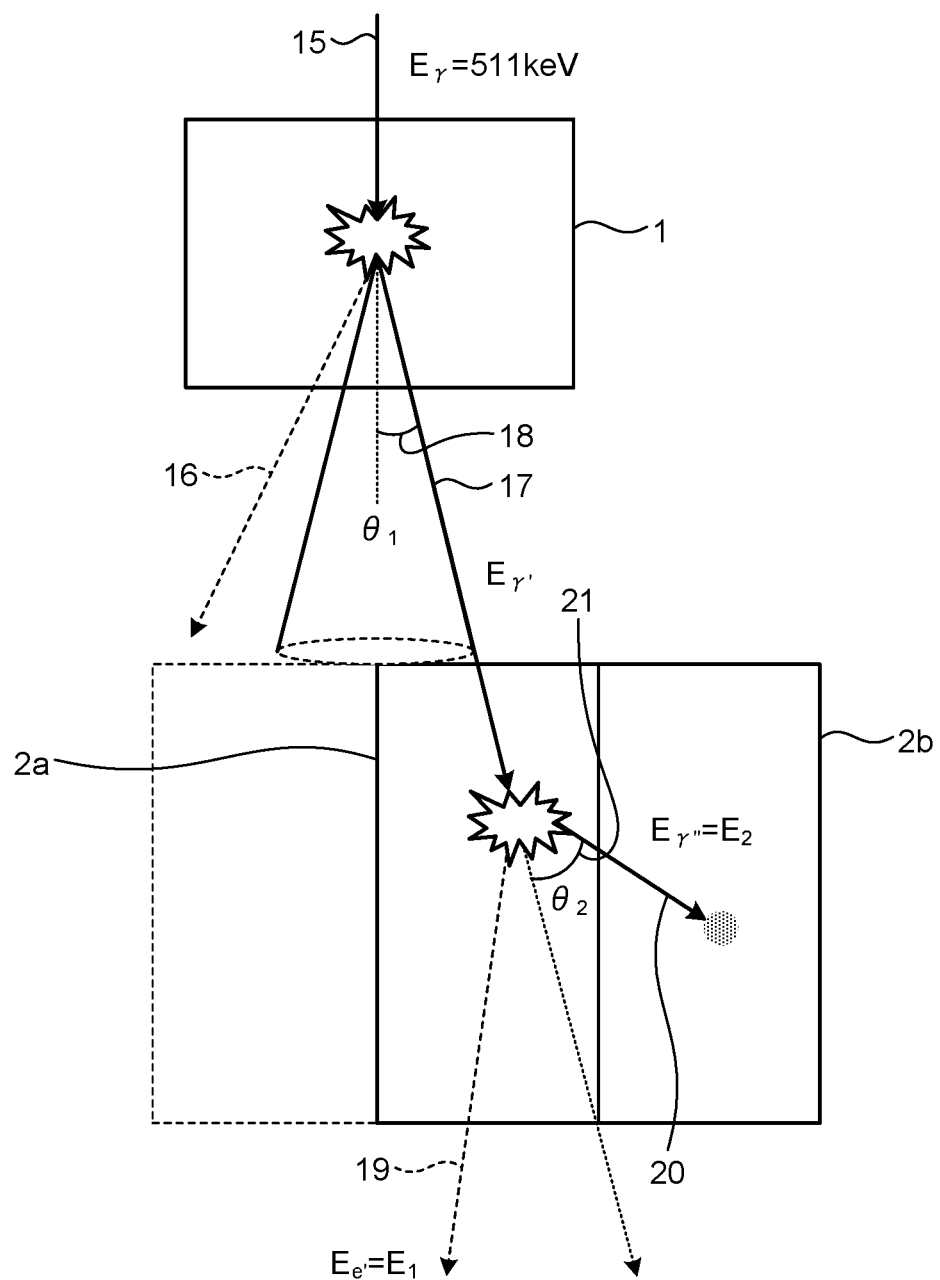
FIG. 5 is a diagram for explaining processing related to the radiation diagnostic device according to the first embodiment.

The following describes this point with reference to FIG. 5.

First, when a pair annihilation gamma ray 15 of 511 keV is incident on the first detector 1, the pair annihilation gamma ray 15 interacts with the first detector 1 to cause Compton scattering, and as a result, a recoil electron 16 is generated. Cherenkov light is generated by the recoil electron 16 moving in a substance. On the other hand, the pair annihilation gamma ray 15 passes part of the energy to the recoil electron 16, so that energy of a gamma ray 17 is changed from the energy of the pair annihilation gamma ray 15. That is, a trajectory of the gamma ray 17 is deviated from a trajectory of the pair annihilation gamma ray 15 by a scattering angle 18.

A value of the scattering angle 18 is typically a relatively small angle, so that the value of the scattering angle 18 may be assumed to be 0 in a case of simply handling the value.

Subsequently, the gamma ray 17 to be an incident gamma ray for the second detector 2a causes Compton scattering in the second detector 2a, and as a result, signals are detected in a plurality of detectors of the second detectors 2. For example, the gamma ray 17 to be the incident gamma ray for the second detector 2 causes Compton scattering in the second detector 2a, and as a result, a recoil electron 19 and a gamma ray 20 are generated. In this case, a trajectory of the gamma ray 20 is deviated from that of the gamma ray 17 to be the incident gamma ray for the second detector 2a by a scattering angle 21. The recoil electron 19 is detected by the second detector 2a, and the gamma ray 20 is detected by the second detector 2b. As a result, signals are detected by both of the second detector 2a and the second detector 2b.

Subsequently, with reference to FIG. 6 and FIG. 7, the following describes a processing procedure of Compton correction performed by a medical image processing device according to the embodiment. First, with reference to FIG. 6, the following describes an overall procedure including processing related to an event of not performing Compton correction. The embodiment can be applied to both of a case in which one of the pair annihilation gamma rays is Compton-scattered, and a case in which both of the pair annihilation gamma rays are Compton-scattered.

First, at Step S100, the processing circuitry 105 acquires timing information and energy information of the pair annihilation gamma ray from the second detector 2 by the acquisition function 105f. In this case, the timing information of the pair annihilation gamma ray in the second detector 2 is, for example, counting information including the scintillator number (P) and the detection time (T). Additionally, the processing circuitry 105 acquires counting information including the energy value (E) of the pair annihilation gamma ray incident on the scintillator by the acquisition function 105f.

Subsequently, at Step S105, the processing circuitry 105 specifies, by the specification function 105a, a Compton scattering event in the second detector 2, that is, an event that has caused a photoelectric effect after Compton scattering in the second detector 2 based on an energy window for Compton scattering correction among events detected by the second detector. That is, the processing circuitry 105 specifies, by the specification function 105a, the Compton scattering event based on energy information, time information, and detection channel information of the event detected by the second detector.

First, the following describes a case in which change in gamma ray energy in the first detector 1 is ignored, and the energy of the gamma ray 17 to be the incident gamma ray for the second detector 2 is assumed to be equal to 511 keV, which is the energy of the pair annihilation gamma ray 15.

In this case, when the energy detected by the second detector 2 falls within a predetermined range from the energy of the pair annihilation gamma ray 15, that is, falls within a predetermined range from 511 keV, the processing circuitry 105 determines, by the specification function 105a, that the event the timing information and the energy information of which are acquired at Step S100 is a normal signal event without Compton scattering, and processing at Step S140 (described later) is performed.

On the other hand, in a case in which signals are observed in a plurality of channels of the second detector 2, and a total value of energy detected by the second detector 2 falls within a predetermined range from the energy of the pair annihilation gamma ray 15, that is, falls within a predetermined range from 511 keV, the processing circuitry 105 determines, by the specification function 105a, that the event the timing information and the energy information of which are acquired at Step S100 is a signal event related to the photoelectric effect after Compton scattering, and pieces of processing at Step S120 to Step S130 are performed. The processing circuitry 105a in a case in which the total value of the energy detected by the second detector 2 does not fall within the predetermined range from the energy of the pair annihilation gamma ray 15, that is, does not fall within the predetermined range from 511 keV, the processing circuitry 105 does not use data of the event for generating a medical image by the specification function 105a.

The processing circuitry 105 may specify, by the specification function 105a, the Compton scattering event in the second detector 2 while considering change in the energy of the gamma ray in the first detector 1, that is, energy change from the pair annihilation gamma ray 15 to the gamma ray 17.

Proceeding to Step S110, among the events detected by the second detector, the processing circuitry 105 performs, by the determination function 105b, the pieces of processing at Step S120 and Step S130 on an event that is determined to be the Compton scattering event by the processing circuitry 105 with the specification function 105a (Yes at Step S110), and estimates a gamma ray incident position in the second detector.

Specifically, first, at Step S120, the processing circuitry 105 specifies and extracts event information in the first detector 1 by the determination function 105b based on the Compton scattering event specified at Step S105 and geometry information of the PET apparatus 100.

That is, assuming that a time at which Cherenkov light is detected by the first detector 1 is $t_1$, a time at which scintillation light is detected by the second detector 2 is $t_2$, and a distance between a place where Cherenkov light is detected by the first detector 1 and a place where scintillation light is detected by the second detector 2 is L, the gamma ray 17 moves in space at a light velocity c, so that, in a case in which a signal detected by the first detector 1 and a signal detected by the second detector 2 are related to the same event, it can be considered that a relation of $L=ct$ is established. For example, by determining whether such a relation is established between the signal detected by the first detector 1 and the signal detected by the second detector 2, the processing circuitry 105 extracts, by the specification function 105a, event information in the first detector 1 corresponding to the Compton scattering event specified at Step S105 while considering the geometry information of the PET apparatus 100 based on the Compton scattering event specified at Step S105. In this case, the event information in the first detector 1 is, for example, a list of the detection element number (P) and the detection time (T). In this way, the processing circuitry 105 extracts, by the determination function 105b, a Cherenkov event corresponding to the Compton scattering event specified at Step S105 based on the time information of the event detected by the first detector and detection channel position information of the first detector.

Subsequently, at Step S130, the processing circuitry 105 estimates, by the determination function 105b, the gamma ray incident position in the second detector 2 based on the event information in the first detector 1 specified at Step S120. That is, the processing circuitry 105 determines, by the determination function 105b, the incident channel of the gamma ray based on the Cherenkov event specified at Step S120. Processing at this step will be described later.

Subsequently, at Step S150, the processing circuitry 105 estimates, by the determination function, the line of response (LOR) based on the gamma ray incident position estimated at Step S130. Processing at this step will also be described later.

Subsequently, at Step S160, the processing circuitry 105 performs, by the image generation function 105c, processing similar to a procedure of generating an image performed by a normal PET apparatus, and generates a medical image based on the LOR estimated at Step S150.

Returning to Step S110, the processing circuitry 105 performs, by the determination function 105b, normal processing on an event other than an event that is determined to be a normal event that is without Compton scattering by the processing circuitry 105 with the specification function 105a (No at Step S110) among the events detected by the second detector, and specifies event information in the first detector corresponding to the event detected by the second detector (Step S140). Specifically, similarly to Step S120, the processing circuitry 105 specifies, by the specification function 105a, the event information in the first detector 1 corresponding to the event specified at Step S100 while considering the geometry information of the PET apparatus 100 based on the event specified at Step S100.

Subsequently, at Step S150, the processing circuitry 105 estimates, by the determination function 105b, the LOR based on the event information specified at Step S140. For example, the processing circuitry 105 estimates, by the determination function 105b, a straight line connecting two detection elements in which Cherenkov light is detected in the first detector to be the LOR.

Subsequently, with reference to FIG. 7, the following describes the pieces of processing at Step S130 and Step S150 in more detail. FIG. 7 is a flowchart for explaining the processing procedure at Step S130 in FIG. 6 in more detail.

First, at Step S131, the processing circuitry 105 estimates, by the determination function 105b, a generated photon number N of Cherenkov light based on signal strength obtained by the first detector 1. That is, the processing circuitry 105 estimates, by the determination function 105b, a Cherenkov photon number related to the Cherenkov event based on the data obtained by the first detector 1.

Subsequently, at Step S132, the processing circuitry 105 estimates, by the determination function 105b, the energy $E_e$ of the recoil electron related to the Cherenkov event based on the generated photon number N (Cherenkov photon number) of Cherenkov light estimated at Step S131.

More specifically, assuming that the generated photon number of Cherenkov light is N, x is a variable representing a thickness in a radial direction of a Cherenkov light detector, $\lambda$ is a wavelength of Cherenkov light, $\alpha$ is a constant, $n(\lambda)$ is a refractive index, v is a velocity of the recoil electron, c is a light velocity, and $n\beta=v/c$, the following expression (3) is established.

$$\frac{dN^2}{dxd\lambda} = \frac{2\pi\alpha}{\lambda^2}\left(1 - \frac{1}{n(\lambda)^2\beta^2}\right) \quad (3)$$

When the expression (3) is integrated for x, the following expression (4) is established assuming that a thickness of the Cherenkov light detector is L.

$$\frac{dN}{d\lambda} = \frac{2\pi\alpha L}{\lambda^2}\left(1 - \frac{1}{n(\lambda)^2\beta^2}\right) \quad (4)$$

In this case, assuming that the wavelength of Cherenkov light that can be detected by the first detector 1 ranges from $\lambda_1$ to $\lambda_2$, the expression (4) is integrated within this range, and the generated photon number N of Cherenkov light generated in the first detector 1 is represented by the following expression (5).

$$N = \int_{\lambda_1}^{\lambda_2} \frac{2\pi\alpha L}{\lambda^2}\left(1 - \frac{1}{n(\lambda)^2\beta^2}\right)d\lambda \simeq 2\pi\alpha L\left(1 - \frac{1}{n^2\beta^2}\right)\left(\frac{1}{\lambda_1} - \frac{1}{\lambda_2}\right) \quad (5)$$

In the expression (5), the generated photon number N of Cherenkov light is associated with the velocity v of the recoil electron 16 via $\beta$ in the expression (5). Thus, by solving the expression (5) for $\beta$, the processing circuitry 105 can estimate, by the determination function 105b, the velocity v of the recoil electron 16 based on the generated photon number N of Cherenkov light. Accordingly, the processing circuitry 105 can estimate, by the determination function 105b, the energy $E_e$ of the recoil electron 16 based on the estimated velocity v of the recoil electron 16.

Subsequently, at Step S133, the processing circuitry 105 calculates, by the determination function 105b, the scattering angle 18 in a first detection channel (first detector 1) based on the energy $E_e$ of the recoil electron 16 estimated at Step S132. Specifically, first, the processing circuitry 105 calculates, by the determination function 105b, energy of the gamma ray 17 and momentum of the gamma ray 17 based on the energy $E_\gamma$ of the pair annihilation gamma ray 15, momentum $p_\gamma$ of the pair annihilation gamma ray 15, the energy $E_e$ of the recoil electron 16, and momentum $p_e$ of the recoil electron 16 by using an energy conservation law and a momentum conservation law. Subsequently, the processing circuitry 105 calculates, by the determination function 105b, the scattering angle 18 based on the calculated energy and momentum of the gamma ray 17.

Subsequently, at Step S134, the processing circuitry 105 determines, by the determination function 105b, an incident channel of the gamma ray 17 in the second detector 2 based on a detection channel of the first detector 1 in which the Cherenkov event is detected and the scattering angle 18 in the detection channel of the first detector 1. Specifically, the processing circuitry 105 determines, by the determination function 105b, the incident channel based on a point at which the second detector 2 intersects with a Compton cone corresponding to the scattering angle 18 and expanded from the detection channel of the first detector 1.

Subsequently, the following describes processing of determining the LOR performed by the processing circuitry 105 with the determination function 105b based on the processing at Step S150 related to the Compton event, that is, determination of the incident channel determined at Step S134.

The following describes processing at Step S134 before describing processing at Step S150. At Step S134, when the processing circuitry 105 determines, by the determination function 105b, the second detector 2a related to the incident channel of the gamma ray 17 among the second detectors 2, the processing circuitry 105 estimates, by the determination function 105b, a process through which a signal value of the second detector 2a and a signal value of the second detector 2b are generated. For example, the processing circuitry 105 estimates, by the determination function 105b, that the signal value generated in the second detector 2a is a signal value resulting from generation of the recoil electron 19 along with Compton scattering caused in the second detector 2a, and is a signal value that is generated due to a photoelectric effect caused by the gamma ray 21 after Compton scattering caused in the second detector 2b. That is, the processing circuitry 105 estimates, by the determination function 105b, energy of the gamma ray 20 after the Compton scattering event based on energy information detected by the second detector 2b as a channel other than the incident channel of the second detector 2, and estimates energy of the recoil electron 19 in the Compton scattering event based on energy information detected by the second detector 2a as the incident channel of the second detector.

Next, at Step S150, the processing circuitry 105 estimates, by the determination function 105b, the LOR based on the generated photon number N of Cherenkov light that is estimated at Step S131 based on the signal value obtained by the first detector 1, the signal value detected by the second detector 2a, and the energy information of the gamma ray detected by the second detector 2b. For example, the processing circuitry 105 estimates, by the determination function 105b, a line connecting detection elements in which Cherenkov light is detected in the first detector 1 as an initial value of the LOR, and calculates predicted values of the generated photon number N of Cherenkov light that is estimated based on the signal value obtained by the first detector 1, the signal value detected by the second detector 2a, and the energy information of the gamma ray detected by the second detector 2b based on the LOR.

Subsequently, the processing circuitry 105 corrects, by the determination function 105b, the LOR by comparing actual measured values with the predicted values of the generated photon number N of Cherenkov light that is estimated based on the signal value obtained by the first detector 1, the signal value detected by the second detector 2a, and the energy information of the gamma ray detected by the second detector 2b, and calculates the LOR that best explains the generated photon number N of Cherenkov light that is estimated based on the signal value obtained by the first detector 1, the signal value detected by the second detector 2a, and the energy information of the gamma ray detected by the second detector 2b as the LOR after correction.

In other words, the processing circuitry specifies Compton scattering events detected by the second detector and determines an event corresponding to a channel that defines an LOR (Line Of Response) or an event corresponding to a channel in which Compton scattering occurred among the specified Compton scattering events based on a detection result obtained by the first detector.

As described above, the radiation detection device according to the first embodiment can generate the counting information while maintaining energy resolution and high time resolution by generating the counting information using the first detector 1 for detecting Cherenkov light and the second detector 2 as a normal detector. The incident position of the gamma ray at the time of Compton scattering can be estimated by the determination unit that determines the event corresponding to the incident channel among the specified Compton scattering events based on the detection result obtained by the first detector, so that a more accurate LOR can be estimated. Due to this, spatial resolution of the PET image can be improved.

Second Embodiment

In the first embodiment, the first detector 1 is assumed to detect Cherenkov light, and the first embodiment does not describe scintillation light and the like that may be detected by the first detector 1 when Compton scattering and the like occur in the first detector 1, for example. However, the embodiments are not limited thereto. In a second embodiment, the first detector 1 detects Cherenkov light that is generated when radiation passes, and also detects scintillation light. The processing circuitry 105 determines, by the determination function 105b, an event corresponding to the incident channel based on Cherenkov light detected by the first detector 1 and scintillation light detected by the first detector 1, and specifies the Compton scattering event detected by the second detector 2.

A detector used as the first detector 1 used for detecting Cherenkov light can also detect scintillation light in many cases, so that the first detector 1 used in the first embodiment can also be used as the first detector 1 according to the second embodiment. In the second embodiment, the first timing information acquisition circuitry 101 detects scintillation light from the first detector 1 in addition to Cherenkov light, and the processing circuitry 105 performs processing including the scintillation light detected from the first detector 1.

The following describes processing according to the second embodiment with reference to FIG. 6 again, and using FIGS. 8 to 11. Regarding FIG. 6, the same processing as that in the first embodiment is performed except for the pieces of processing at Steps S120 to S160, so that the redundant description will not be repeated.

Similarly to the first embodiment, at Step S120, the processing circuitry 105 specifies and extracts, by the determination function 105b, event information in the first detector 1 based on the Compton scattering event specified at Step S105 and the geometry information of the PET apparatus 100. In the second embodiment, the first detector 1 detects scintillation light in addition to Cherenkov light that is generated when radiation passes. That is, the processing circuitry 105 acquires, by the acquisition function 105f, a detector output signal including a Cherenkov light component and a scintillation light component from the first detector 1 through the first timing information acquisition circuitry 101.

Subsequently, at Step S130, the processing circuitry 105 estimates, by the determination function 105b, the gamma ray incident position in the second detector 2 based on event information of Cherenkov light and scintillation light in the first detector 1 specified at Step S120.

Figure 7:
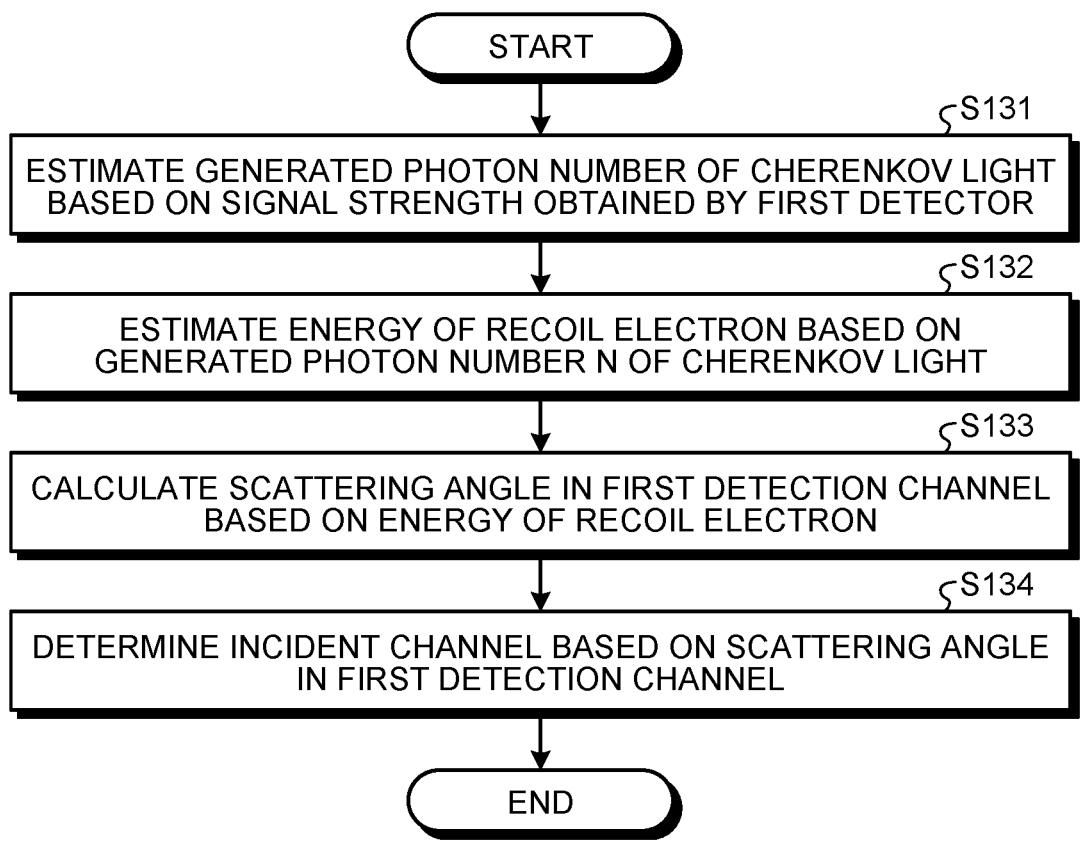
FIG. 7 is a flowchart for explaining a processing procedure at Step S130 in FIG. 6 in more detail.
Figure 8:
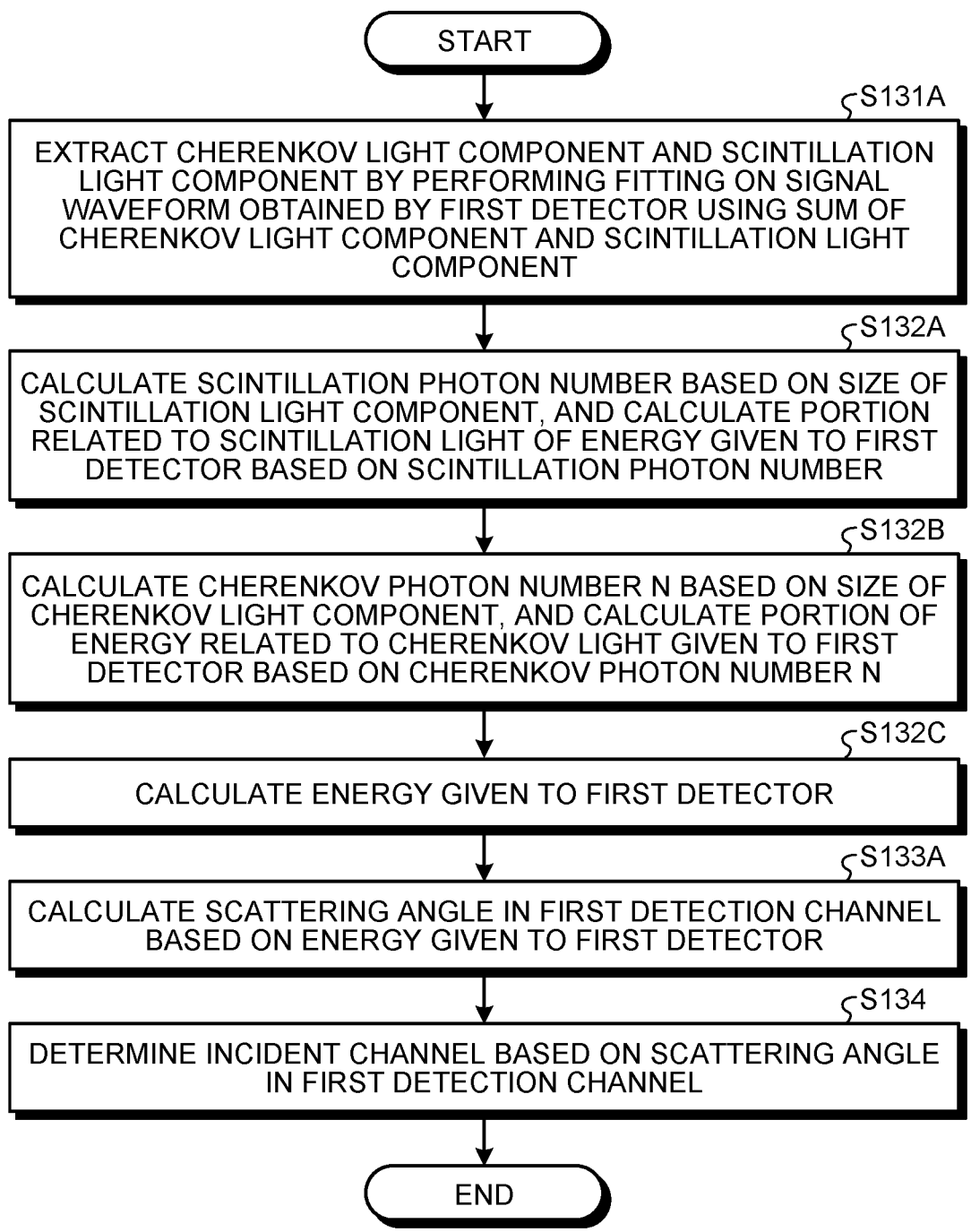
FIG. 8 is a diagram for explaining a processing procedure at Step S130 according to a second embodiment.

The following describes processing at Step S130 according to the second embodiment with reference to FIG. 8. FIG. 8 is a flowchart for explaining a processing procedure at Step S130 according to the second embodiment. As compared with FIG. 7 for explaining the processing procedure at Step S130 according to the first embodiment, the same processing is performed at Step S134 in both of FIG. 7 and FIG. 8. In the second embodiment, pieces of processing at Step S131A to Step S133A are performed in place of the pieces of processing at Step S131 to Step S133 in FIG. 7 according to the first embodiment. The processing at Step S134 is the same as that in the first embodiment, so that the redundant description will not be repeated.

At Step S131A, the processing circuitry 105 extracts, by the determination function 105b, the Cherenkov light component and the scintillation light component from the detector output signal including the Cherenkov light component and the scintillation light component that is acquired at Step S120.

Figure 9:
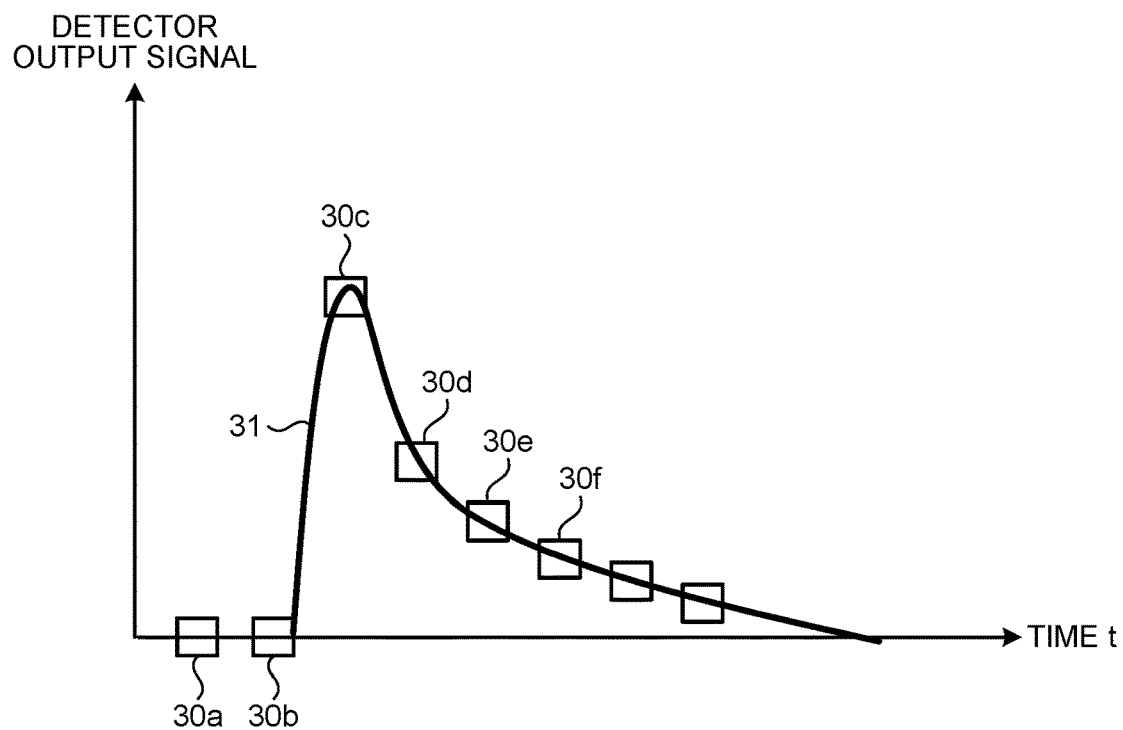
FIG. 9 is a diagram for explaining processing according to the second embodiment.
Figure 10:
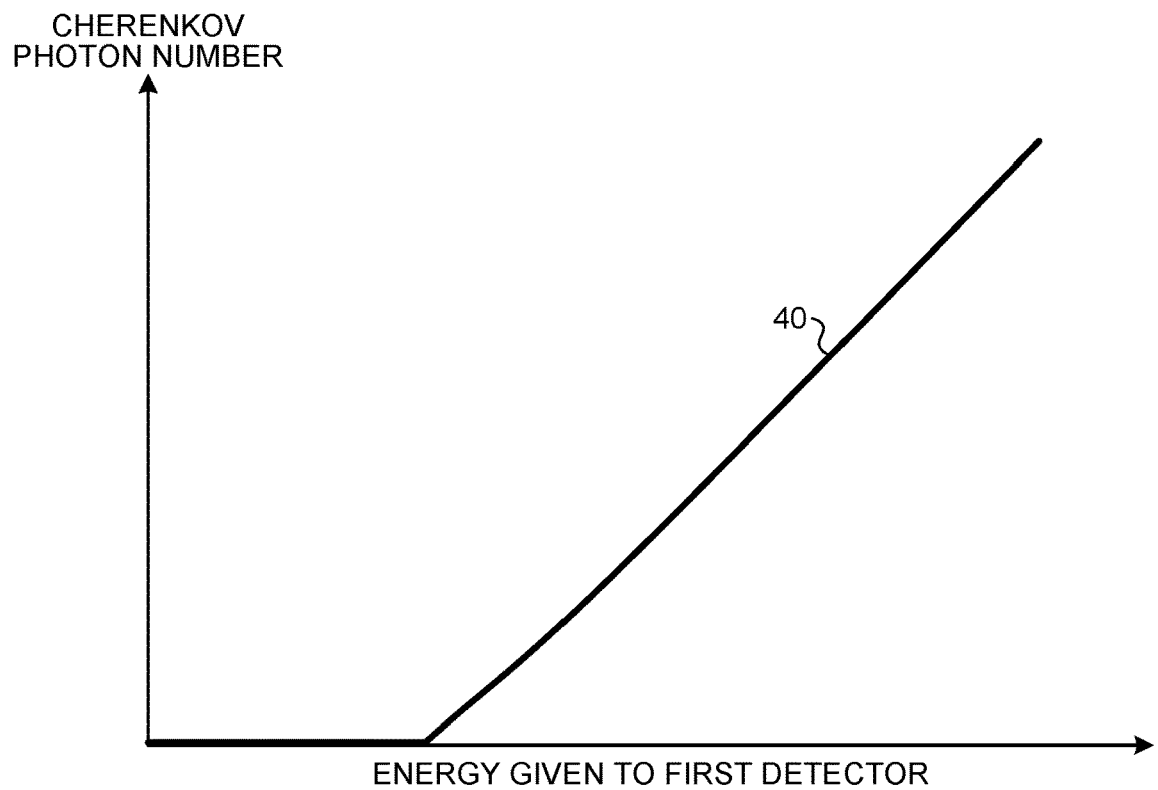
FIG. 10 is a diagram for explaining processing according to the second embodiment.

FIG. 9 illustrates a signal waveform of the detector output signal output from the detector 1. Each of signals 30a, 30b, 30c, 30d, 30e, 30f, and the like indicates an output signal that is sampled at each time illustrated in FIG. 9. By the determination function 105b, processing circuitry 150 estimates parameters using function F given by the following expression (6), for example, on a detector output waveform 31 obtained from these signals 30a to 30f and the like.

$$F(\alpha, \beta, t) = \alpha \cdot f(t) + \beta \cdot g(t) \quad (6)$$

In this case, F is the detector output waveform 31, t is the time, f(t) is a known function representing the scintillation light component included in the detector output waveform 31, $\alpha$ is a parameter representing a size of the scintillation light component included in the detector output waveform 31, g(t) is a known function representing the Cherenkov light component included in the detector output waveform 31, and $\beta$ is a parameter representing a size of the Cherenkov light component included in the detector output waveform 31. In this way, the processing circuitry 105 extracts, by the determination function 105b, the Cherenkov light component and the scintillation light component by estimating parameters, by expressing the detector output waveform 31 that is a signal waveform obtained by the first detector 1 as a sum of the Cherenkov light component and the scintillation light component.

Subsequently, at Step S132A, the processing circuitry 105 calculates, by the determination function 105b, a scintillation photon number based on the size α of the scintillation light component obtained at Step S132B, and calculates a portion related to the scintillation light of the energy given to the first detector 1 by radiation based on the calculated scintillation photon number.

Subsequently, at Step S132B, the Cherenkov photon number N is calculated by the calculation function 105b based on the size β of the Cherenkov light component obtained at Step S131A. Subsequently, the processing circuitry 105 calculates, by the calculation function 105b, a portion related to Cherenkov light of the energy given to the first detector 1 by radiation based on the Cherenkov photon number N.

For example, the Cherenkov photon number N that is generated when the gamma ray gives energy $E_{dep}$ to a radiator is given by the following expression (7) according to the Frank-Tamm formula.

$$\frac{dN}{dE_{dep}} = 2A\pi\alpha Z^2 \left(\frac{1}{\lambda_1} - \frac{1}{\lambda_2}\right)\left(1 - \frac{1}{\beta^2 n^2}\right) \quad (7)$$

In this case, A is a proportional count representing stopping power, α is a fine structure constant (1/137), Z is an electric charge of a charged particle that causes Cherenkov radiation, $\lambda_1$ and $\lambda_2$ are both ends of a visible light wavelength of Cherenkov radiation, and n is a refractive index of a medium.

β is a relative velocity of a charged particle in a substance with respect to a photon velocity in a vacuum, and the following expression (8) is established between β and the energy $E_{dep}$ given to the first detector 1.

$$\beta = \sqrt{1 - \left(\frac{1}{\frac{E_{dep}}{m_0 c^2} + 1}\right)^2} \quad (8)$$

In this case, $m_0$ is a rest mass of an electron, and c is a light velocity.

By solving a differential equation obtained by substituting the expression (8) for the expression (7), given is a relation between the Cherenkov photon number N and the energy $E_{dep}$ given to the first detector 1 by the gamma ray. Specifically, the following expression (9) is approximately established.

$$N(E_{dep}) = \begin{cases} 0 & \text{for } E_{dep} < E_{th} \\ \gamma(E_{dep} - E_{th}) & \text{for } E_{dep} \geq E_{th} \end{cases} \quad (9)$$

In this case, $E_{th}$ is an energy threshold, and γ is a predetermined coefficient. The expression (9) described above can be illustrated as in FIG. 10. A graph 40 represents a relational expression between the Cherenkov photon number N and the energy $E_{dep}$ given to the first detector 1. At Step S132B, the processing circuitry 105 calculates, by the calculation function 105b, the energy $E_{dep}$ as a portion related to Cherenkov light out of the energy given to the first detector 1 based on the relation between the Cherenkov photon number N and the energy $E_{dep}$ given to the first detector 1, and the Cherenkov photon number N.

Returning to FIG. 8, at Step S132C, the processing circuitry 105 calculates, by the calculation function 105b, the energy given to the first detector 1. By way of example, the processing circuitry 150 calculates, by the calculation function 105b, the energy given to the first detector 1 by adding up the portion related to scintillation light out of the energy given to the first detector 1 calculated at Step S132A and the portion related to Cherenkov light out of the energy given to the first detector 1 calculated at Step S132B.

Subsequently, at Step S133A, the processing circuitry 105 calculates, by the calculation function 105b, the scattering angle in the first detection channel based on the energy given to the first detector 1 calculated at Step S132C. Specifically, the expression (1) as an energy conservation law and the expression (2) representing a relation between the scattering angle and the energy before and after Compton scattering are described to be related to the second detector 2, but the same expressions are established also in a case in which Compton scattering occurs in the first detector 1. Thus, by applying the expressions (1) and (2) described above to a case in which similar scattering occurs in the first detector 1, the processing circuitry 105 can calculate, by the calculation function 105b, the scattering angle in a case in which Compton scattering occurs in the first detector 1 based on the energy given to the first detector 1 calculated at Step S132C, and calculates the scattering angle in the first detection channel based thereon.

Subsequently, at Step S134, by performing the same processing as that in the first embodiment, the processing circuitry 105 determines, by the determination function 105b, the incident channel based on the scattering angle in the first detection channel. In this way, at Step S131A to Step S134, the processing circuitry 105 separates a signal waveform obtained by the first detector 1 into the Cherenkov light component and the scintillation light component, and determines the event corresponding to the incident channel based on the separated Cherenkov light component and the scintillation light component by the determination function 105b.

Returning to FIG. 6, at Step S150, similarly to the first embodiment, the processing circuitry 105 determines, by the determination function 105b, the LOR based on the incident channel determined at Step S134.

Subsequently, at Step S160, similarly to the first embodiment, the processing circuitry 105 performs, by the image generation function 105c, the same processing as a normal image generation procedure of the PET apparatus, and generates a medical image based on the LOR estimated at Step S150.

For an event other than the event that is determined to be a normal event without Compton scattering by the processing circuitry 105 with the specification function 105a among the events detected by the second detector at Step S110 (No at Step S110), the processing circuitry 105 specifies, by the determination function 105b, event information in the first detector 1 corresponding to the event detected by the second detector (Step S140). In this case, in specifying the event information in the first detector, the processing circuitry 105 may use information about scintillation light obtained by the first detector 1, or does not necessarily use the information for the processing at Step S140.

As described above, in the second embodiment, the Compton scattering event is corrected by using both of Cherenkov light and scintillation light detected by the first detector 1. Due to this, spatial resolution of the PET image can be improved.

Other Embodiments

Some embodiments have been described above, but the embodiments are not limited thereto. In the embodiment, the processing circuitry 105 specifies a generation event of scintillation light in the second detector 2 first, and specifies the event information in the first detector 1 corresponding thereto. However, the embodiment is not limited thereto.

Figure 6:
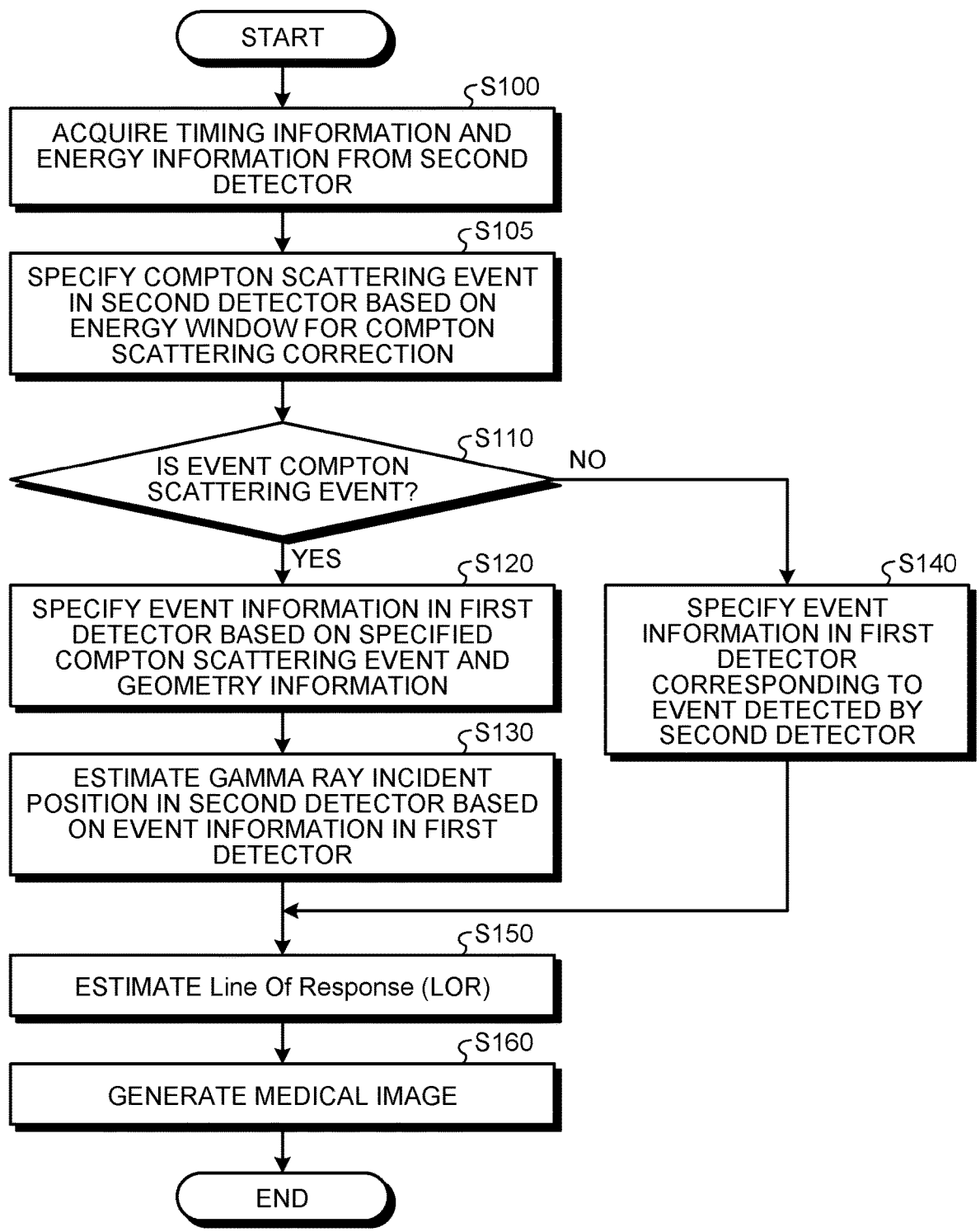
FIG. 6 is a flowchart for explaining a processing procedure performed by the radiation diagnostic device according to the first embodiment.

By way of example, at a step previous to Step S100 in FIG. 6, the processing circuitry 105 specifies, by the acquisition function 105f, event information of the Cherenkov event from the first detector 1. Subsequently, the processing circuitry 105 specifies, by the specification function 105a, the event information including the Compton scattering event detected by the second detector corresponding to the Cherenkov event acquired by the acquisition function 105f based on the event information of the Cherenkov event specified from the first detector 1 and the geometry information of the PET apparatus 100. The processing circuitry 105 may acquire, by the acquisition function 105b, the specified event information in the second detector to perform the processing at Step S100. In this way, by specifying the event information earlier in the first detector 1 having excellent time resolution, estimation efficiency for the LOR can be improved.

According to at least one of the embodiments described above, image quality can be improved.

Regarding the embodiments described above, the following notes are disclosed as an aspect and an optional characteristic of the invention.

Note 1. A radiation diagnostic device comprising:
a first detector configured to detect Cherenkov light that is generated when radiation passes;
a second detector disposed to be opposed to the first detector on a side distant from a generation source of the radiation and configured to detect energy information of the radiation;
a specification unit configured to specify Compton scattering events detected by the second detector; and
a determination unit configured to determine an event corresponding to an incident channel among the specified Compton scattering events based on a detection result obtained by the first detector.

Note 2. The specification unit may specify the Compton scattering event based on energy information, time information, and detection channel information of the event detected by the second detector.

The determination unit may extract a Cherenkov event corresponding to the specified Compton scattering event based on time information of an event detected by the first detector and detection channel position information of the first detector, and determine the incident channel based on the Cherenkov event.

Note 3. The determination unit may determine the incident channel based on a detection channel of the first detector in which the Cherenkov event is detected and a scattering angle in the detection channel of the first detector.

Note 4. The determination unit may estimate a Cherenkov photon number related to the Cherenkov event based on data obtained by the first detector, estimate energy of a recoil electron related to the Cherenkov event based on the Cherenkov photon number, and detect the scattering angle based on the energy of the recoil electron.

Note 5. The determination unit may determine the incident channel based on a point at which the second detector intersects with a Compton cone, corresponding to the scattering angle, expanded from the detection channel of the first detector.

Note 6. The determination unit may estimate energy of a gamma ray after the Compton scattering event based on energy information that is detected in a channel other than the incident channel of the second detector, and estimate energy of the recoil electron in the Compton scattering event based on energy information detected in the incident channel of the second detector.

Note 7. The radiation diagnostic device may further comprise an acquisition unit configured to acquire the Cherenkov event from the first detector.

The specification unit may specify a Compton scattering event detected by the second detector corresponding to the Cherenkov event acquired by the acquisition unit.

Note 8. The determination unit may estimate an LOR based on energy information detected in a channel other than the incident channel, energy information detected in the incident channel, and data obtained by the first detector.

Note 9. The determination unit may estimate the LOR based on energy information detected in a channel other than the incident channel and data obtained by the first detector.

Note 10. The determination unit may estimate the LOR based on energy information detected in the incident channel and data obtained by the first detector.

Note 11. The first detector may further detect scintillation light, and
the determination unit may determine an event corresponding to the incident channel based on the scintillation light and the Cherenkov light detected by the first detector.

Note 12. The determination unit may separate a signal waveform obtained by the first detector into a Cherenkov light component and a scintillation light component, and determine an event corresponding to the incident channel based on the separated Cherenkov light component and the scintillation light component.

Note 13. The determination unit may separate the signal waveform obtained by the first detector into the Cherenkov light component and the scintillation light component by estimating parameters using a sum of the Cherenkov light component and the scintillation light component.

Note 14. The determination unit may specify Compton scattering events detected by the second detector and determine an event corresponding to a channel that defines an LOR (Line Of Response) among the specified Compton scattering events based on a detection result obtained by the first detector.

Note 15. The determination unit may specify Compton scattering events detected by the second detector and determines an event corresponding to a channel in which Compton scattering occurred among the specified Compton scattering events based on a detection result obtained by the first detector.

Note 16. A correction method for a Compton scattering event comprising:
specifying Compton scattering events detected by a second detector disposed to be opposed to a first detector on a side distant from a generation source of the radiation and configured to detect energy information of radiation, the first detector being configured to detect Cherenkov light that is generated when the radiation passes; and
determining an event corresponding to an incident channel among the specified Compton scattering events based on a detection result obtained by the first detector.

Note 17. A computer program product having a computer readable medium including programmed instructions, wherein the instructions, when executed by a computer, cause the computer to perform processing of:

specifying Compton scattering events detected by a second detector disposed to be opposed to a first detector on a side distant from a generation source of the radiation and configured to detect energy information of radiation, the first detector being configured to detect Cherenkov light that is generated when the radiation passes; and determining an event corresponding to an incident channel among the specified Compton scattering events based on a detection result obtained by the first detector.

Note 18. A non-transitory computer readable medium being a computer program product storing programmed instructions, wherein the instructions, when executed by a computer, cause the computer to perform processing of:

specifying Compton scattering events detected by a second detector disposed to be opposed to a first detector on a side distant from a generation source of the radiation and configured to detect energy information of radiation, the first detector being configured to detect Cherenkov light that is generated when the radiation passes; and determining an event corresponding to an incident channel among the specified Compton scattering events based on a detection result obtained by the first detector.

What is claimed is:

1. A radiation diagnostic device comprising:
   a first detector configured to detect Cherenkov light that is generated when radiation passes;
   a second detector disposed to be opposed to the first detector on a side distant from a generation source of the radiation and configured to detect energy information of the radiation; and
   processing circuitry configured to specify Compton scattering events detected by the second detector, and determine an event corresponding to an incident channel among the specified Compton scattering events based on a detection result obtained by the first detector.

2. The radiation diagnostic device according to claim 1, wherein the processing circuitry:
   specifies a Compton scattering event based on energy information, time information, and detection channel information of an event detected by the second detector, and
   extracts a Cherenkov event corresponding to the specified Compton scattering event based on time information of an event detected by the first detector and detection channel position information of the first detector, and determines the incident channel based on the Cherenkov event.

3. The radiation diagnostic device according to claim 2, wherein the processing circuitry determines the incident channel based on a detection channel of the first detector in which the Cherenkov event is detected and a scattering angle in the detection channel of the first detector.

4. The radiation diagnostic device according to claim 3, wherein the processing circuitry estimates a Cherenkov photon number related to the Cherenkov event based on data obtained by the first detector, estimates energy of a recoil electron related to the Cherenkov event based on the Cherenkov photon number, and detects the scattering angle based on the energy of the recoil electron.

5. The radiation diagnostic device according to claim 3, wherein the processing circuitry determines the incident channel based on a point at which the second detector intersects with a Compton cone, corresponding to the scattering angle, expanded from the detection channel of the first detector.

6. The radiation diagnostic device according to claim 3, wherein the processing circuitry estimates energy of a gamma ray after the Compton scattering event based on energy information detected in a channel other than the incident channel of the second detector, and estimates energy of a recoil electron in the Compton scattering event based on energy information detected in the incident channel of the second detector.

7. The radiation diagnostic device according to claim 1, wherein the processing circuitry:
   acquires a Cherenkov event from the first detector, and
   specifies a Compton scattering event detected by the second detector corresponding to the acquired Cherenkov event.

8. The radiation diagnostic device according to claim 1, wherein the processing circuitry estimates a line of response (LOR) based on energy information detected in a channel other than the incident channel and data obtained by the first detector.

9. The radiation diagnostic device according to claim 8, wherein the processing circuitry estimates the LOR based on energy information detected in a channel other than the incident channel, energy information detected in the incident channel, and data obtained by the first detector.

10. The radiation diagnostic device according to claim 1, wherein the processing circuitry estimates a line of response (LOR) based on energy information detected in the incident channel and data obtained by the first detector.

11. The radiation diagnostic device according to claim 1, wherein
    the first detector further detects scintillation light, and
    the processing circuitry determines an event corresponding to the incident channel based on the scintillation light and the Cherenkov light detected by the first detector.

12. The radiation diagnostic device according to claim 11, wherein the processing circuitry separates a signal waveform obtained by the first detector into a Cherenkov light component and a scintillation light component, and determines an event corresponding to the incident channel based on the Cherenkov light component and the scintillation light component.

13. The radiation diagnostic device according to claim 1, wherein the processing circuitry specifies Compton scattering events detected by the second detector and determines an event corresponding to a channel that defines an LOR (Line Of Response) among the specified Compton scattering events based on a detection result obtained by the first detector.

14. The radiation diagnostic device according to claim 1, wherein the processing circuitry specifies Compton scattering events detected by the second detector and determines an event corresponding to a channel in which Compton scattering occurred among the specified Compton scattering events based on a detection result obtained by the first detector.

15. A correction method for a Compton scattering event, comprising:
    specifying Compton scattering events detected by a second detector disposed to be opposed to a first detector on a side distant from a generation source of radiation, the second detector being configured to detect energy information of radiation, the first detector being configured to detect Cherenkov light that is generated when the radiation passes; and determining an event corresponding to an incident channel among the specified Compton scattering events based on a detection result obtained by the first detector.

16. A non-transitory computer-readable medium being a computer program product storing programmed instructions, wherein the programmed instructions, when executed by a computer, cause the computer to perform processing of:

specifying Compton scattering events detected by a second detector disposed to be opposed to a first detector on a side distant from a generation source of radiation, the second detector being configured to detect energy information of radiation, the first detector being configured to detect Cherenkov light that is generated when the radiation passes; and determining an event corresponding to an incident channel among the specified Compton scattering events based on a detection result obtained by the first detector.

* * * * *